(12) United States Patent
Hardt (10) Patent No.: US 10,039,471 B2
(45) Date of Patent: Aug. 7, 2018

(54) ISOCHRONIC TONE AUGMENTED BIOFEEDBACK SYSTEM

(71) Applicant: James V. Hardt, Sedona, AZ (US)

(72) Inventor: James V. Hardt, Sedona, AZ (US)

(*) Notice: Subject to any disclaimer, the term of this patent is extended or adjusted under 35 U.S.C. 154(b) by 401 days.

(21) Appl. No.: 14/759,494

(22) PCT Filed: Jan. 24, 2014

(86) PCT No.: PCT/US2014/012934
§ 371 (c)(1),
(2) Date: Jul. 7, 2015

(87) PCT Pub. No.: WO2014/116939
PCT Pub. Date: Jul. 31, 2014

(65) Prior Publication Data
US 2015/0342493 A1 Dec. 3, 2015

Related U.S. Application Data

(60) Provisional application No. 61/757,034, filed on Jan. 25, 2013.

(51) Int. Cl.
*A61B 5/04* (2006.01)
*A61B 5/0482* (2006.01)
*A61B 5/048* (2006.01)
*A61B 5/00* (2006.01)

(52) U.S. Cl.
CPC ............ *A61B 5/0482* (2013.01); *A61B 5/048* (2013.01); *A61B 5/742* (2013.01); *A61B 5/7405* (2013.01); *A61B 5/7455* (2013.01)

(58) Field of Classification Search
CPC ... A61B 5/0482; A61B 5/0484; A61B 5/0476; A61B 5/7405; A61B 5/7455
See application file for complete search history.

(56) References Cited

U.S. PATENT DOCUMENTS

| | | | |
|---|---|---|---|
| 4,334,545 | A | 6/1982 | Shiga |
| 4,928,704 | A | 5/1990 | Hardt |
| 5,036,858 | A | 8/1991 | Carter |
| 5,356,368 | A | 10/1994 | Monroe |
| RE36,348 | E | 10/1999 | Carter |
| 6,481,703 | B2 | 11/2002 | Yoshida et al. |
| 8,340,753 | B2 | 12/2012 | Hardt |
| 2006/0030907 | A1 | 2/2006 | McNew |
| 2006/0116597 | A1 | 6/2006 | Vesely |
| 2006/0116598 | A1 | 6/2006 | Vesely |
| 2006/0116600 | A1 | 6/2006 | Vesely |
| 2006/0252978 | A1 | 11/2006 | Vesely |
| 2006/0252979 | A1 | 11/2006 | Vesely |

(Continued)

*Primary Examiner* — Christian Jang
(74) *Attorney, Agent, or Firm* — Bert P. Krages, II (57) ABSTRACT

A biofeedback system that utilizes isochronic tone technology to augment EEG feedback by providing to a subject isochronic tones at the frequency of a targeted aspect of a subject's brain waves, such as the brain's naturally occurring peak energy in the particular EEG band or bands subject to the biofeedback. Isochronic tones are regular beats of a single tone that are formed by separate pulses of sound and silence. In addition, feedback can be provided to the subject in the form of pulsed light and pulsed tactile impulses that are delivered in the form of alternating presence and absence of light or tactile pressure.

20 Claims, 4 Drawing Sheets

(56) References Cited

U.S. PATENT DOCUMENTS

2011/0105938 A1* 5/2011 Hardt .................. A61B 5/0482
  600/544
2011/0298706 A1* 12/2011 Mann ..................... G06F 3/015
  345/157
2012/0150545 A1   6/2012 Simon

* cited by examiner

ISOCHRONIC TONE AUGMENTED BIOFEEDBACK SYSTEM

TECHNICAL FIELD

The invention relates generally to an apparatus and method for monitoring electroencephalography (EEG) activity for use in biofeedback training.

DESCRIPTION OF THE INVENTION

The invention is an improvement and extension of the EEG biofeedback methods and systems as set forth in U.S. Pat. No. 4,928,704 and U.S. Pat. No. 8,340,753, which are fully incorporated by reference into this application. This application claims the benefit to the prior U.S. Patent application 61/757,034 filed Jan. 25, 2013, the filing date of which is hereby claimed and which application is hereby adopted by reference as part of the present disclosure. Note that "EEG biofeedback" is also described in the literature as neurofeedback, neurobiofeedback, biofeedback or simply as feedback. The improvement and extension to the biofeedback system is to incorporate isochronic tone technology to augment the EEG biofeedback provided to the subject. Isochronic tones are regular beats of a single tone that are formed by separate pulses of sound and silence. In addition, feedback can be provided to the subject in a visual form such as pulses of light and pulses of tactile pressure that are delivered in the form of alternating presence and absence of a visual stimulus or tactile pressure. Thus, the descriptions of the auditory pulses can also be understood to be applied in an analogous manner for visual stimuli and pulses of tactile pressure.

This EEG biofeedback system comprises either one or a pair of reference electrodes, a suitable ground electrode, and a plurality (number=N) of active cortical site electrodes that are placed on the head of a subject with output signals directed to an equal number (N) of EEG amplifiers. The output of each of the active cortical site electrodes is filtered into sub-bands or sub-ranges of the EEG. The filtered signals can be converted into aural, visual, or tactile response indicia and supplied in real time to the subject to allow the subject to respond instantaneously to biofeedback signals. The system contemplates that at least 17 frequency sub-bands (and preferably more) may be established: (1) slow delta, (2) fast delta, (3) broad band delta, (4) slow theta, (5) fast theta, (6) broad band theta, (7) slow alpha, (8) middle alpha, (9) fast alpha, (10) broad band alpha, (11) slow beta, (12) fast beta, (13) broad band beta, (14) slow gamma, (15) fast gamma, (16) broad band gamma and (17) the Schumann frequency between 7-8 Hz. Frequency-domain filtering is accurately effected by the system with minimal delay and with great accuracy and precision, and additional narrower filter bands can be established to give finer resolution in the frequency domain. It is also possible to do Fast Fourier Transforms (FFTs) with very fine frequency resolution to give information on precisely which frequency within a band of interest (delta, theta, alpha, beta, or gamma) has the peak amplitude or peak energy at any given moment of time.

Important features of the EEG biofeedback system are that it (a) permits easy recognition of specific sub-bands and sub-ranges of the EEG; (b) permits easy recognition of peak amplitude or peak energy within the chosen sub-bands or sub-ranges and easy recognition of other aspects of peak performance within the chosen sub-bands or sub-ranges; (c) permits recognition of the presence or absence of artifact conditions; (d) facilitates association of these recognitions with an often transient mental or subjective state accompanying them; (e) permits recognition of the presence or absence of desired signal conditions ("signal" being the desired EEG activity or absence of activity upon which they are doing neurofeedback); (f) facilitates association of these recognitions with an often transient mental or subjective state accompanying them and (g) facilitates the attainment of stable mental or subjective states, which are associated with underlying EEG activity, which EEG activity is the subject of the biofeedback training.

A primary benefit of the invention is that it facilitates learning self-control of one's own EEG activity through EEG biofeedback and by isochronic-tone enhanced (or augmented) EEG biofeedback and it helps and enables subjects to learn control over their mental and emotional and spiritual subjective states and their underlying physiological states of their brain activity. The goal of such self-control is not confined to obtaining control of the measurable EEG parameters, but goes well beyond that to obtaining self-control of the mental and emotional and spiritual subjective states associated with the objectively measurable EEG sub-bands and sub-ranges.

The parameters for producing the isochronic tone are the isochronic frequency, the tone pitch, and amplitude of the tone and the percentage of the cycle during which the isochronic tone is on and off. It is often useful to have the tone-on time be less than a half cycle of the isochronic frequency. Specifically, the system provides isochronic tones at the frequency of a targeted aspect of a subject's brain waves, such as the brain's naturally occurring peak energy in the particular EEG band or bands subject to the biofeedback. This frequency of peak energy changes dynamically and rapidly in the brains of most people, so that the frequency at which the peak amplitude occurs in one instant may not be the frequency at which the peak amplitude occurs in the next instant. For example, alpha at 12 cycles per second could slow within one cycle to become alpha at 8 cycles per second.

Isochronic-tone augmented EEG feedback can be done for brain waves of any brain frequency band or range such as delta, theta, alpha, beta, or gamma bands or ranges. For example, the frequency range of alpha is 8-13 cycles per second and a person's alpha activity could be anywhere in that range. A person's alpha is not fixed at a stable frequency, and the frequency drifts and sometimes shifts suddenly, slowing and then speeding up again, or speeding up and then slowing again. In this invention, the EEG activity is analyzed to make a nearly instantaneous determination of the frequency at which the peak energy in the chosen feedback band, say for example the alpha band, is occurring. Any means suitable for analysis of the EEG signals could be used to determine this frequency of the instantaneous peak energy, examples include Fast Fourier Transforms (FFTs) or very narrow band digital filtering. As soon as the frequency having the maximum energy is determined, that frequency is used to determine the details of the isochronic-tone enhancement for augmenting the EEG biofeedback that is currently being provided to the subject. Whenever the frequency of the peak energy in the alpha (or other band or bands of interest) changes, then that new frequency would be detected, analyzed, and used to determine the frequency that would receive isochronic-tone augmentation of the EEG feedback training currently underway.

It is also possible to use the isochronic-tone enhanced EEG feedback in the spirit of this invention to augment frequencies other than that frequency at which the peak energy is occurring instantaneously. It may be that after some measurement period (a baseline) with or without EEG feedback, that a frequency can be identified, within the EEG band of interest, which, over time, has the greatest average energy or amplitude. This frequency could then be selected as the frequency to receive isochronic tone enhancement to the neurofeedback process. In addition to this alternative method of determining the frequency to receive isochronic-tone enhancement to the neurofeedback process, there can also be other useful methods employed, such as selecting the frequency with the lowest detectable amount of energy or amplitude. This could be either the lowest average energy or the lowest detectable energy at any given moment. Statistical analysis of the energy distribution across the frequency bands or range of interest can also be used to select frequencies for use in isochronic-tone augmentation of neurofeedback, and these could include, but not be limited to, the centroid of the frequency x amplitude diagram, or the mean or the median of observed frequencies that are then weighted, or not, by amplitude, energy, or temporal abundance.

Isochronic tones have been associated with an EEG frequency entrainment response in the brain where its period of a particular brain wave will correspond to the fundamental frequency of the stimulus. In other words, providing tones having a particular isochronic frequency can result in entrainment in which brain wave activity is driven toward a predetermined state, i.e. the frequency at which the isochronic tone is occurring. Thus, providing isochronic tones to the brain can be a form of external control that can stimulate the production of brain waves that are not naturally occurring in the brain. Prior art implementations of isochronic tones involve stimulating production of brain wave frequencies that are not naturally occurring in that brain or at least not in that brain at that time. However, by processing the EEG signal to determine the frequency at which the person's the peak energy is occurring at each moment, the isochronic tone can be tailored to precisely follow, moment-by-moment, the brain's naturally occurring frequencies of peak energy, or other brain wave frequencies that exist within the brain, and thus can be used to enhance the biofeedback provided by the EEG biofeedback system. When used in this form, the augmentation provided by the isochronic tone will not induce the production of brain waves that are not naturally occurring (no invasive frequencies). This could thus be an ethical use of isochronic-tone augmented neurofeedback that may effectively avoid the type of interventions that impose artificial states that are not indigenous to that brain receiving the feedback.

All of the augmentation of EEG activity produced by the isochronic tone process will be of EEG activity that is already naturally occurring in the brain at that moment, or has occurred recently with detectable amplitudes. It is desirable to provide the biofeedback as quickly as possible, preferably within one-half second of the emission of the brain wave. Indeed, the EEG activity that is being augmented by isochronic tones in one preferred implementation is that EEG activity that is in each moment, the EEG activity of the peak energy. This methodology can be seen as more organic and more in harmony with the natural ecology of the brain's own naturally-occurring frequency patterns. This isochronic-tone augmented EEG feedback system enables the subject to enhance the production of the desired and targeted brain wave activity by two processes simultaneously. The one process is the natural process of the brain responding to EEG feedback signals in one or more sensory modalities, with the brain then increasing the amplitude and temporal abundance of the desired and targeted EEG frequencies, and the second process is the isochronic tone augmentation of brain activity that occurs at the EEG frequency that matches the frequency or frequencies of the isochronic tone, which in one preferred implementation is given only at the naturally-occurring frequencies of the brain that have the peak energy in every moment. Isochronic-tone augmented biofeedback can thus be useful in various applications including those in which people who do not have much naturally-occurring activity (e.g. low amplitude and low abundance) in a particular brain wave band such as alpha or theta, and in teaching people with very large amplitudes of desirable brain wave patterns to develop even larger amplitudes and greater abundances of their most desirable brain wave patterns.

DETAILED DESCRIPTION OF PREFERRED EMBODIMENTS

Figure 1:
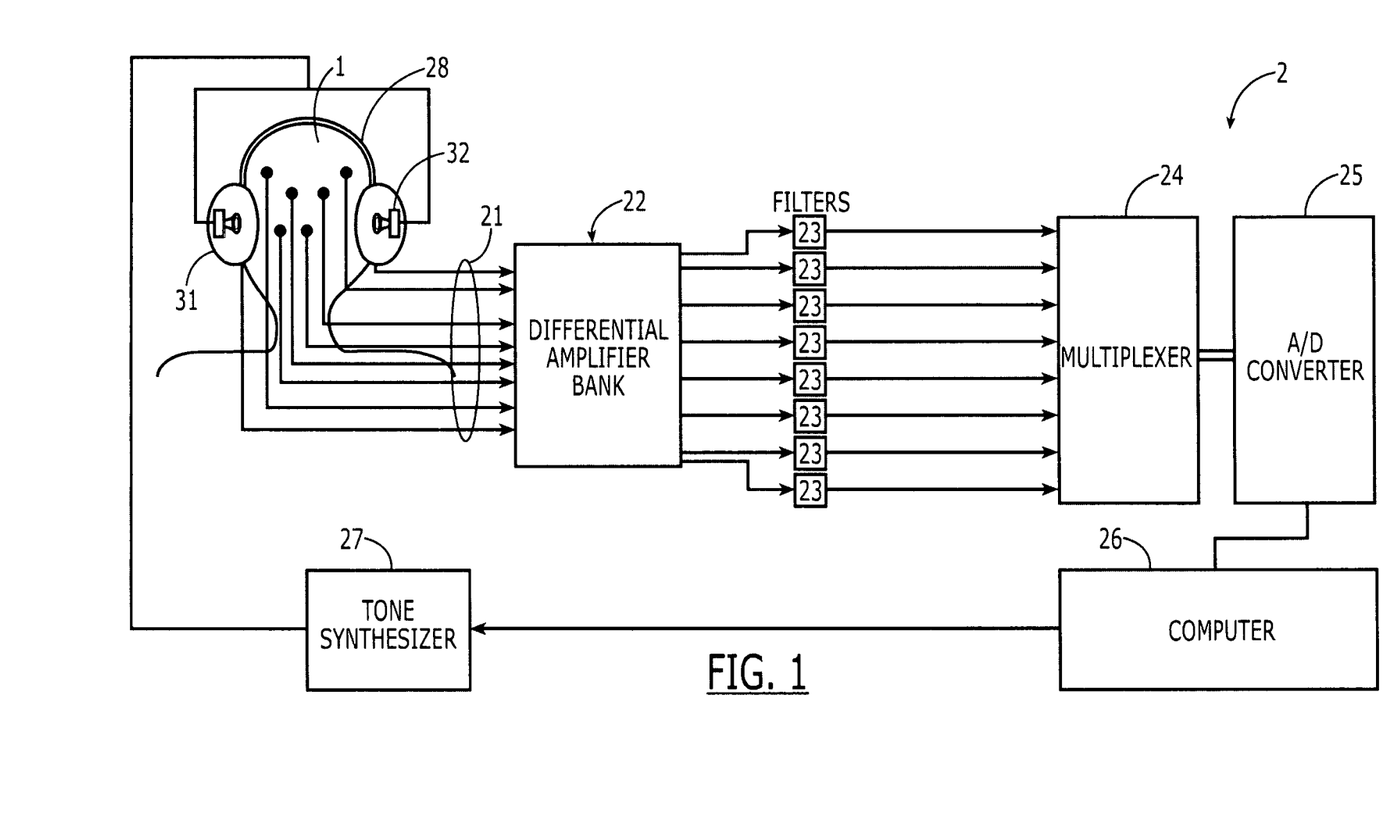
FIG. 1 is a diagram showing the subject and the biofeedback apparatus.

Referring to FIG. 1, in the preferred audio feedback embodiments, the subject 1 is connected to provide input to the apparatus 2 through EEG leads 21 and to receive audio output from the apparatus 2 through stereo headphones 28. On the head of the subject 1 are mounted a plurality of EEG leads 21 including a pair of reference electrodes attached to the ear lobes, a suitable ground electrode, and a plurality of active cortical site electrodes mounted in lateral pairs and used in monopolar configuration. The output signals directed to an equal number of EEG amplifiers in an EEG amplifier bank 22. The output of each of the active cortical site electrodes is amplified and filtered into sub-bands or sub-ranges of the EEG in a corresponding number of multiple channel filter banks 23, and thereafter through a multiplexer 24 to a analog-to-digital converter 25. It is preferred to use high input impedance, low noise, low drift operational amplifiers, low current drain amplifiers to permit optional use with battery power sources. Elimination of line voltage power increases common mode rejection by eliminating all coupling to the 60 Hz AC line.

In the preferred embodiments, the EEG amplifier bank 23 contains analog bandpass filters in sets of eight. The bandpass filters according to the invention may be active and are characterized by an elliptical response with 300-400 dB per octave rolloff at the skirts, 0.25 dB ripple in the pass-band and at least 50 dB rejection in the stop band. The filters have a pass-band of only a few hertz. The filter sets spectrally decompose the EEG signals through its input from an electrode into a plurality of sub-bands. The sub-bands may be chosen according to the training level of the subject and object of the training.

In the preferred audio-feedback embodiments, the filters are configured to select the specific sub-bands: delta (2.0-3.5 Hz), slow theta (4.2-5.4 Hz), fast theta (5.5-6.8 Hz), slow alpha (7.5-8.8 Hz), broadband alpha (7.7-12.6 Hz), fast alpha (10.8-12.9 Hz), slow beta (14.2-17.2 Hz), and broadband beta (15.0-24.0 Hz). Alternative bands or sub-bands may be designated, such as broadband theta (4.0-6.7 Hz), middle alpha (8.9-10.7 Hz), and fast beta (17.3-24.0 Hz). Under selected conditions, only a few of the sub-bands are processed and made available as feedback signals. The outputs of each filter set may be made available as (a) filtered EEG, (b) filtered, full-wave rectified EEG, and (c) filtered, full-wave rectified and smoothed EEG.

The outputs are fed into a multiple-channel multiplexer 24. The multiplexer 24 in turn directs the signals as analog samples to the 12-bit analog-to-digital converter 25. In this embodiment, a microcomputer 26 is provided for real-time processing of the output digital samples although such processing could alternatively be done by a mainframe computer or one or more dedicated microprocessors. Note that the microcomputer 26 encompasses the typical devices associated with microcomputers such as a keyboard and mouse input devices, one or more monitors, one or more printers, memory, and a central processing unit. The microcomputer 26 serves a variety of control and data recording functions and the peripherals provide conventional input and output functions in support of the control and analysis functions of the microcomputer 26. One such function of the microcomputer 26 is to evaluate the digital signals to determine the amplitude of the peak energy within the selected band or sub-band and the frequency at which that peak energy occurs. Digital processing software such as those using a fast Fourier transform (FFT) algorithm can be run on the microcomputer 26 to implement this function. For example, the peak energy frequency can be used to set the frequency of the isochronic tone provided as the neurofeedback. As the frequency changes, it becomes the new frequency at which the isochronic tone is set.

The microcomputer 26 sends a signal representative of the amplitude and frequency of the peak energy within the desired band or sub-band to a tone synthesizer 27. The purpose of the tone synthesizer 27 is to create the isochronic tone signal which is sent to speaker 31 and speaker 32. In one preferred audio-feedback embodiment, these speakers are mounted in stereo headphones 28 that are worn by the subject 1. The signal generator may be internal to the computer or may be an external device such as the tone synthesizer 27 just described. When the signal is used to actuate a device that creates visual or tactile stimuli, the signal sent by the microcomputer 26 may be sufficient to control the visual or tactile stimuli generating device in which case microcomputer 26 itself serves as the signal generator. For example, subsequent processing of the signal might not be necessary when the stimuli generating device consists of means such as LEDs or vibrators.

Figure 2:
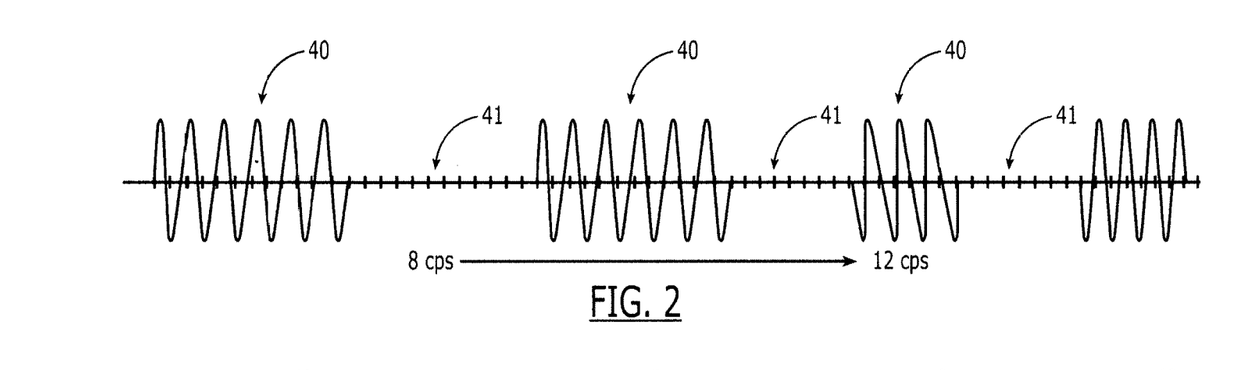
FIG. 2 is a diagram showing a representation of a progression of a generated isochronic tone having the form of a sine wave.
Figure 3:
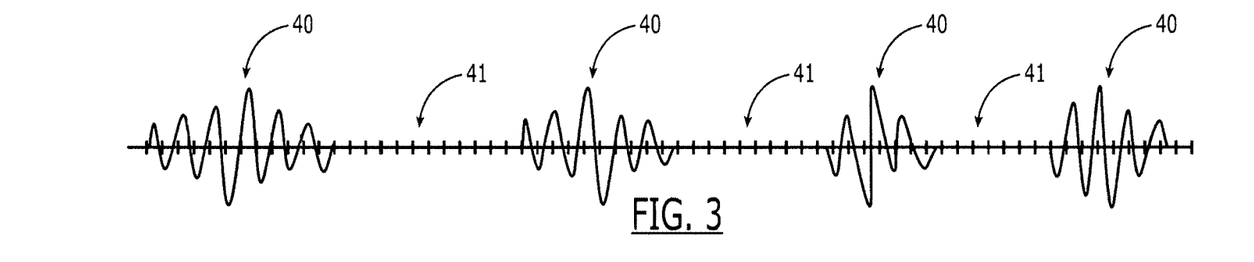
FIG. 3 is a diagram showing a representation of a progression of a generated isochronic tone having the form of a sine wave with increasing and decreasing amplitude.
Figure 4:
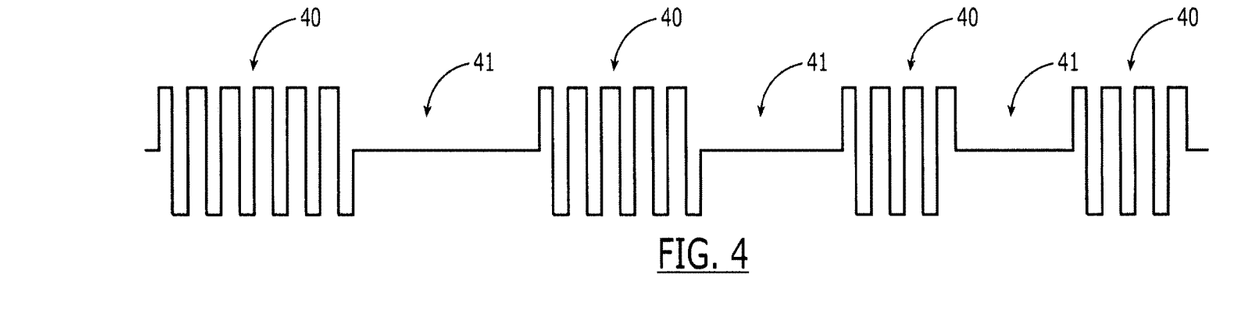
FIG. 4 is a diagram showing a representation of a progression of a generated isochronic tone having the form of a square wave.

An example of a progression of the generated isochronic tone signal is shown in FIG. 2 as the brain wave frequency increases from 8 cycles per second to 12 cycles per second. The tone synthesizer produces a tone having a sound portion 40 and a silent portion 41. In the preferred embodiments, the sound portion 40 may be selectively generated in the wave form that is judged to be the most effective for inducing entrainment. In FIG. 2, a sine wave of constant amplitude is depicted. In addition, the volume can be made proportional to the amplitude of the brain wave signal received from the EEG apparatus. This can allow the subject to monitor both the frequency and intensity of the brain wave of interest. For example, the amplitude of the tone feedback can be proportional to the amplitude of the instantaneous filtered EEG. as shown in FIG. 3 in which the amplitude of the sound portion 40 of the signal increases and then decreases. However, the amplitude of the tone feedback need not be linearly related to the amplitude of the instantaneous filtered EEG, but rather could be made proportionally louder when the amplitude of the instantaneous filtered EEG is lower (to provide more entrainment "boost" when the amplitude of the instantaneous filtered EEG is low) and could be made proportionally less loud when the amplitude of the instantaneous filtered EEG is higher (since there may be less need for entrainment in those moments where the amplitude of the instantaneous filtered EEG is higher). The wave form of sound portion may be of various forms such as the square wave (shown in FIG. 4), sawtooth, and triangle wave forms.

One aspect of the invention is that the sound transmitted to the subject may be provided in different variations in order to enhance entrainment or at least minimize disruptive effects. For many subjects, wave forms encompassing near instantaneous changes in amplitude, such as square waves, tend be more entraining. However, such waves tend to have a staccato nature that some subjects find irritating. The scope of the invention includes different ways to address this issue to make the tones more pleasant and tolerable to sensitive subjects. For instance, it is common to synthesize tones so that the durations of the sound portion and silent portion are equal. For instance, when alpha is at 11 cycles per second, such a system would set the duration of the sound portion of the wave at 0.0455 seconds and the duration of the silent portion likewise at 0.0455 seconds, and thus the frequency at which the isochronic tone pulsates will be the same as the alpha brain wave frequency (i.e., 11 cycles per second). However, the degree of staccato experienced by a subject can be modified by making the duration of the sound portion less than the duration of the silent portion (or vice versa). An example would be to set the duration of the sound portion at 0.0100 seconds and the duration of the silent portion at 0.081 seconds so that the frequency is 11 cycles per second but with a lower duration of the sound portion. Conversely, the duration of the sound portion could constitute the major portion of the cycle. When such tone is programmed to vary in accordance with wave forms in which the amplitude rises and falls more or less gradually, the perceived effect can be that of fuzzy beats which are better tolerated by some subjects than staccato beats.

As stated previously, the volume of the tone varies depending on the amplitude of the brain wave at the selected frequency band, i.e., the entire alpha band or some sub-band within the alpha band. It can be also desirable to set a minimum volume for the tones to ensure that the subject is able to hear them at all times during a session. Should a signal have insufficient amplitude to produce an audible feedback tone, it may be amplified to the level associated with a preselected minimum volume. Conversely, a maximum volume can be set to ensure that the feedback is limited to a level the subject finds comfortable.

Because isochronic tones are generated and perceived as a actual tone, as opposed to binaural beats, in which different but steady tones delivered to each ear produce a tone that is perceived to have a beat, there is no need to use headphones. However, headphones can be useful in situations where experimentation with different kinds and forms of tones is desired. For example, it is possible to set up a tone synthesizer so that it receives signals reflecting brain wave activity from different bands or subbands and this generates two tones having different isochronic frequencies which in turn can be delivered to the subject via separate headphone speakers. Similarly, offset isochronic beats having the same frequency but different cycle timing can be delivered via separate headphone speakers.

Figure 5:
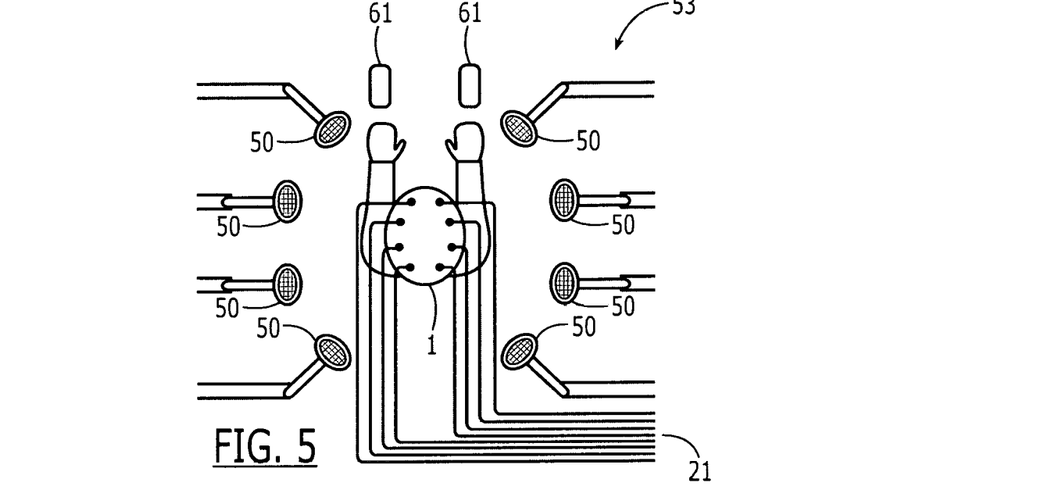
FIG. 5 is a diagram depicting a setup with a plurality of audio speakers and light bars.
Figure 6:
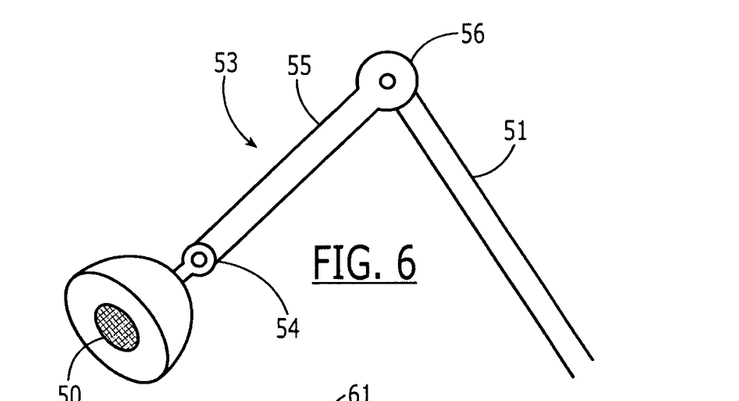
FIG. 6 is a diagram depicting a speaker mounted on a swing arm.

However, a more versatile means of enhancing the transmission of tones to the subject is shown in FIG. 5 using multiple speakers surrounding the subject 1 to which EEG leads 21 have been attached. Preferably, the speakers are mounted on adjustable swing arms 53 so that speakers 50 may be selectively positioned in an array around the subject. FIG. 6 depicts an example of a swing arm 53 showing a speaker 50 attached via a articulating joint 54 to a rod 55 which is in turn is attached by another articulated joint 56 to another rod 51. Although the system requires only a single speaker to transmit sound to the subject, the ability to position a plurality of speakers can enhance versatility and effectiveness. In a typical deployment in which eight active cortical site electrodes are placed on the head of a subject, eight speakers can be arranged such that each is placed around the head so as to generally correspond in location to the brain lobe monitored by a site electrode. In such disposition, because the different lobes of the brain can emit brain waves at different frequencies, the placement of multiple speakers in a relative manner enables the provision of multiple tones in accordance with the frequencies being emitted by the particular brain lobes or areas of scalp being monitored by an electrode. In addition, the use of multiple speakers allows for tones to be transmitted at different phases and for different classes of brain wave frequencies to be transmitted simultaneously (e.g., alpha and theta).

The signals can also be processed to produce a visual stimulus or graphic reflecting the biofeedback or to produce a tactile output through means such as a vibrating or pneumatic device. Such variations could be used alone or in conjunction with the audio feedback tones to motivate and accelerate learning of EEG self-regulation and self-control. In particular, it is considered desirable to augment the feedback with visual feedback provided by a light source capable of intermittently emitting pulses of light. The frequency at which the light pulses are emitted as well as the intensity of the light pulses can be controlled by signals processed in a manner analogous to that done for isochronic tones.

Figure 7:
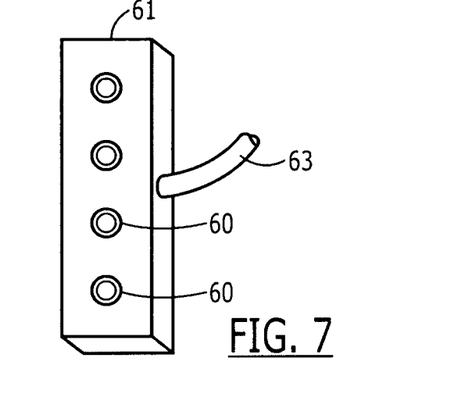
FIG. 7 is a diagram depicting a light bar.

In another preferred embodiment, the light would be pulsed by providing processed signals to one or more light sources such as light-emitting diodes (LEDs). In the embodiment, as shown in FIG. 7, LEDs 60 are mounted in a box structure 61 connected to the computer via a cable 63. As shown in FIG. 5, the box structure 61 can be placed in front of the subject so that it is visible during a session. It can be particularly desirable to provide a pair of box structures, preferably attached or adjacent to the front-most speakers as depicted in FIG. 6. Ideally, the banks of LEDs are placed about 21 inches apart. Alternatively, the LEDs could be mounted within goggles so as to minimize outside visual distractions. It is desirable that the intensity of the light not be strong enough to cause discomfort to the subject or overwhelm the audio feedback (when used in conjunction with audio feedback).

LEDs of different colors may be used, although in a preferred basic embodiment, the preferred color is blue. However, for certain applications it may be desirable to use LEDs having other colors or multiple colors. In a preferred advanced embodiment, each LED is associated with a signal from a different electrode and can emit pulses of light as directed by such signal. For example, blue LEDs could emit pulses associated with brain waves originating from the frontal lobes, green LEDs could emit pulses associated with brain waves originating from the occipital lobes, and so on. Other means of applying signal processing can also be used. For instance, the signals from the electrodes could be processed so that the signals sent to the LEDs are based on the type of brain wave. An example of this would be having blue LEDs emit pulses of light based on the subjects alpha brain wave activity while red LEDs emit pulses based on the gamma brain wave activity.

Figure 8:
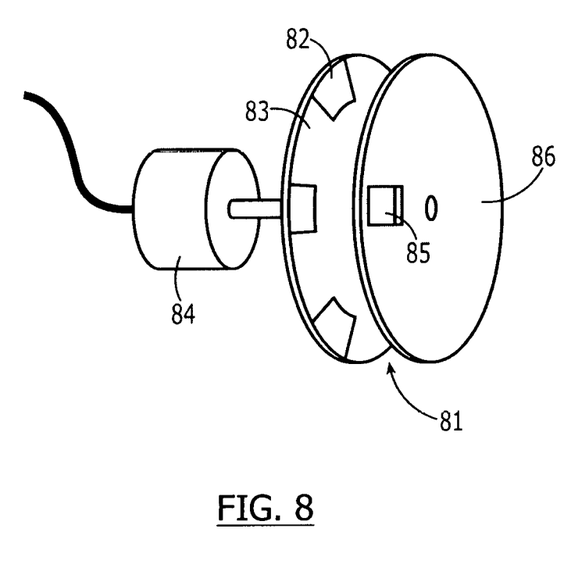
FIG. 8 is a diagram depicting an optical output device.

It should be noted that LEDs, or even other devices that generate light, are not the only means by which a visual stimulus may be delivered to a subject. Other means by which visual stimuli may be delivered in a isochronic manner include devices in which a shutter opens and closes in accordance to isochronic timing or in which alternating images are presented to an opening visible to the subject in an isochronic manner. For example, as shown in FIG. 8, a disc 81 having alternating arcs of differing colors or shades 82 and 83 can be rotated by a motor 84 at a revolution rate controlled in accordance with the isochronic frequency so that such colors or shades are made visible through an opening 85 in a plate 86 such that the subject perceives the change in color or shade at the isochronic frequency being monitored.

It is highly desirable to minimize the delay between the sensing of an EEG event and the presentation of that event to the subject in the form of a tone. According to the invention, the feedback delay should be less than about 500 ms and preferably less than 350 ms to optimize feedback training. In one preferred embodiment, the feedback delay is less than 100 ms, which is less than one alpha wave cycle.

This process of isochronic-tone augmented EEG feedback can be done on just one of the EEG channels (and thus just one or one set of the head sites) of the EEG feedback process and that channel could be the channel with the greatest amplitude or the lowest amplitude or any other channel or combinations of channels of interest. The process could also be done on a plurality of channels simultaneously, since the EEG biofeedback system can function using multiple channels simultaneously. Note that while the EEG biofeedback system encompasses the ability to simultaneously monitor and to provide EEG feedback on multiple channels, the isochronic-tone augmentation contemplated by this improvement could also be used in a single channel device and that this invention encompasses both single-channel and multiple channel embodiments.

Many people find they benefit most from multichannel EEG feedback training when they focus their attention on the one or two channels with the greatest amplitude. In such cases, the other weaker channels will follow along and demonstrate better performance than if the person had focused attention during neurofeedback on the weaker channels. However with isochronic-tone augmentation of the EEG feedback, there could well be a change in that standard practice, in which the isochronic-tone augmented neurofeedback (ICANF) is productively used to boost the weakest one or two channels of a multi-channel montage. When training for increased amplitude, it is quite reasonable to develop strategies of using ICANF that are related to the initial ranking of the amplitudes of each channel, so emphasizing working with the largest or the smallest amplitude will be the most reasonable approach in the majority of cases, but it is possible that some applications would benefit from selecting specific channels, selecting intermediate channels based on predetermined parameters such as rate of brain wave fluctuation, and the like.

Although peak energy is typically the best parameter on which to base the feedback, the system could be keyed off of some fraction of a brain wave band or sub-band other than the part associated with the peak energy. For example, the average or median energy could be used. While one of the preferred embodiments is based on selection based on the peak energy to avoid substantial interference with the naturally-established brain wave patterns of subjects, other embodiments could make selections based on non-peak energy levels albeit with some possible risk to the subject caused by disruption to their normal brain wave patterns.

The method of using the system is readily discernable from the description above and the incorporated references. In any case, one of the basic forms of the method comprises the following steps:

(a) placing EEG sensors on cortical sites on the head of a person;
(b) sensing electric potentials from the cortical sites to obtain a signal for a selected brainwave;
(c) selecting the particular aspect of the brainwave signal to be processed (e.g., peak energy, greatest average energy, lowest detectable energy);
(d) processing the signal to determine the frequency of the selected aspect of the signal according to a training program;
(e) using the frequency of the preselected aspect of the signal to determine the frequency at which the isochronic tone should be set; and
(f) monitoring the brain wave signal and processing on a continuing basis to instantaneously provide the feedback to the person to indicate to the person the EEG activity at the cortical sites in order to facilitate voluntary conscious and unconscious control over said personal EEG activity.

In most cases, it will be desirable to place the person in an environment of controlled light and sound (e.g., dark and quiet) to control the arousal level and the distractibility of the person. Generally speaking, when feedback is provided by both audio and non-audio means, the two means should be synchronized with the sound volume and light intensity proportional to each other. However, providing audio and non-audio feedback in asynchronous or inversely proportional manners may be useful in certain applications. For example, providing tones generated from signals processed from different areas of the brain in an asynchronous manner could avoid the unintentional and incidental perception of binaural beats caused by tones having close but distinctly different frequencies.

Baseline testing can be conducted prior to a biofeedback session. Typically, an "eyes open" baseline is then run which is designed to reveal the subject's minimal alpha levels and to allow the operator to check out and calibrate all instruments. The eyes open baseline run is generally in the presence of bright light and with a steady background tone provided by headphones set to the frequency of tone that will be created by the tone synthesizer. However, the baseline can be modified so that tones and LEDs are run in different modes to test for disruptive effects. Examples are using different wave forms for the tones, different colors for LEDs, using combinations of feedback from different bands or subbands, and varying the synchronicity and intensity of the feedback. If desired, adjustments can be made in order to make the training comfortable for the subject. Following the "eyes open" baseline assessment, an "eyes closed" baseline can then run in a similar manner to determine the nature of brainwave activity in the absence of conventional stimuli. This is typically conducted in darkness. A "white noise" baseline can also be run in preparation for the actual training sessions. The white noise run is used to condition the subject to attend to an audio signal while allowing the mind to relax without loss of recollection ability. White or quasi-white Gaussian noise is provided by the headphones. Data collected during the baseline assessments are collected with respect to the amplitude and energy frequencies of the brainwave activity and stored into the memory of a computer.

As will be apparent to a person skilled in the art, a number of variations and modifications can be made to the system and method described above without departing from the spirit and scope of the present invention. All such modifications and variations are contemplated as being within the scope of the invention.

I claim:

1. A method for training a person to augment desirable personal electroencephalographic (EEG) activity, said method comprising the steps of:
    (a) securing EEG leads to the person;
    (b) receiving an EEG signal from the person;
    (c) transmitting the resultant EEG signal to a filter;
    (d) filtering the EEG signal;
    (e) monitoring a predetermined EEG frequency band or subband;
    (f) determining the EEG frequency value of a preselected aspect of said EEG signal;
    (g) using a signal generator to generate an isochronic signal in a form perceptible by the person, in which the frequency of the signal is set at the value of said EEG frequency value; and
    (h) delivering said isochronic signal to said person with minimal delay between receiving the EEG signal and delivery of the isochronic signal.

2. The method of claim 1 wherein said preselected aspect is the EEG frequency value at which the peak energy of the EEG signal occurs.

3. The method of claim 1 in which said isochronic signal is delivered to said person in an audio form in which the sound portion has a shorter duration than the silent portion.

4. The method of claim 1 in which said isochronic signal is delivered to said person in visual form which comprises a plurality of lights having different colors in which each light is associated with a signal from a preselected EEG lead.

5. The method of claim 1 in which said isochronic signal is delivered to said person in visual form which comprises a plurality of lights having different colors in which each color is associated with a type of brain wave being monitored.

6. The method of claim 1 wherein said preselected aspect is the EEG frequency value at which the peak energy of the EEG signal occurs and in which said isochronic signal is delivered to said person in audio form in which the sound portion has a shorter duration than the silent portion.

7. The method of claim 1 wherein said preselected aspect is the frequency at which the greatest average energy of the EEG signal occurs over a preselected interval of time.

8. The method of claim 1 wherein said preselected aspect is the frequency at which the greatest average energy of the EEG signal occurs over a preselected interval of time and in which said isochronic signal is delivered to said person in audio form in which the sound portion has a shorter duration than the silent portion.

9. The method of claim 1 wherein said preselected aspect is the frequency at which the greatest average energy of the EEG signal occurs over a preselected interval of time and in which said isochronic signal is delivered to said person in visual form which comprises a plurality of lights having different colors in which each light is associated with a signal from a preselected EEG lead.

10. The method of claim 1 wherein said preselected aspect is the frequency at which the greatest average energy of the EEG signal occurs over a preselected interval of time and in which said isochronic signal is delivered to said person in visual form which comprises a plurality of lights having different colors in which each color is associated with a type of brain wave being monitored.

11. The method of claim 1 wherein said preselected aspect is the frequency at which the lowest detectable energy of the EEG signal occurs over a preselected interval of time.

12. The method of claim 1 wherein said preselected aspect is the frequency at which the lowest detectable energy of the EEG signal occurs over a preselected interval of time and in which said isochronic signal is delivered to said person in audio form in which the sound portion has a shorter duration than the silent portion.

13. An apparatus for training a person to develop useful degrees of voluntary control of personal electroencephalographic (EEG) activity, said apparatus comprising:
(a) a plurality of EEG sensors, said sensors being for placement at a plurality of cortical sites on a head of said person;
(b) amplifiers coupled to said EEG sensors to amplify a plurality of channel signals in a plurality of channels;
(c) a plurality of bandpass filters coupled to said amplifiers having a passband characteristic of a predefined frequency spectra having an abrupt cutoff at a low-frequency skirt, an abrupt cutoff at a high-frequency skirt and near instantaneous propagation for processing in accordance within time constraints limited by natural neurological reactivity to obtain a resultant signal for each said channel;
(d) a computing device to perform the operation of determining an EEG frequency value based on a preselected aspect of one or more of the resultant signals;
(e) a signal generator receiving input from said computing device and generating an isochronic tone at the EEG frequency value, said signal generator having the capability of generating said isochronic tone such that the sound portion has a shorter duration than the silent portion; and
(f) a means of delivering said isochronic signal to said person.

14. The apparatus of claim 13 wherein said preselected aspect is the frequency at which the peak energy of the EEG signal occurs.

15. The apparatus of claim 13 wherein the means of delivering said isochronic tone to said person is a speaker.

16. The apparatus of claim 13 wherein said preselected aspect is the frequency at which the peak energy of the EEG signal occurs and the means of delivering said isochronic tone to said person is a speaker.

17. The apparatus of claim 13 wherein said preselected aspect is the frequency at which the greatest average energy of the EEG signal occurs over a preselected interval of time.

18. The apparatus of claim 13 wherein said preselected aspect is the frequency at which the greatest average energy of the EEG signal occurs over a preselected interval of time and the means of delivering said isochronic tone to said person in audio form is a speaker.

19. The apparatus of claim 13 wherein said preselected aspect is the frequency at which the lowest detectable energy of the EEG signal occurs over a preselected interval of time.

20. A method for training a person to augment naturally-occurring personal electroencephalographic (EEG) activity, said method comprising the steps of:
(a) securing EEG leads to a plurality of cortical sites on the person;
(b) receiving EEG signals from the EEG leads;
(c) filtering the EEG signals;
(d) monitoring one or more predetermined EEG frequency bands or subbands for each EEG signal;
(e) determining the EEG frequency value of a preselected aspect of each of the EEG signals;
(f) generating a plurality of isochronic signals, each of which is associated with the signal from one of the EEG leads; and
(g) delivering each of the isochronic signals in audio form by a speaker disposed adjacent to the cortical site from which the EEG signal associated with the isochronic signal is derived.

\* \* \* \* \*